United States Patent [19]

Kobayashi

[11] Patent Number: 5,374,760

[45] Date of Patent: Dec. 20, 1994

[54] FLUORINE-CONTAINING ORGANOSILICON COMPOUNDS AND METHOD FOR THE PREPARATION THEREOF

[75] Inventor: Hideki Kobayashi, Chiba, Japan

[73] Assignee: Dow Corning Toray Silicone Co., Ltd., Tokyo, Japan

[21] Appl. No.: 213,396

[22] Filed: Mar. 14, 1994

[30] Foreign Application Priority Data

Mar. 31, 1993 [JP] Japan .................................. 5-096592

[51] Int. Cl.$^5$ ................................................ C07F 7/08
[52] U.S. Cl. ................................ 556/448; 556/487
[58] Field of Search ........................... 556/448, 487

[56] References Cited

U.S. PATENT DOCUMENTS

| | | | |
|---|---|---|---|
| 3,012,006 | 12/1961 | Holbrook et al. | 556/487 |
| 3,331,813 | 7/1967 | Pittman et al. | 556/448 |
| 4,089,882 | 5/1978 | Takamizawa et al. | 260/448.2 E |
| 4,968,828 | 11/1990 | Yamamoto | 556/448 |

FOREIGN PATENT DOCUMENTS 140787 8/1982 Japan .
255288 10/1988 Japan .

*Primary Examiner*—Paul F. Shaver
*Attorney, Agent, or Firm*—Alexander Weitz

[57] ABSTRACT

A fluorine-containing organosilicon compound and a method for its preparation are disclosed, said compound having the general formula $$C_mF_{(2m+1)}-R^2-\underset{\underset{H_a}{|}}{Si}R^1_{(3-a)}$$

in which $R^1$ represents a monovalent hydrocarbon group, excluding alkenyl group, $R^2$ represents a divalent organic group, $a$ is 2 or 3, and $m$ is an integer having a value of 4 to 12.

12 Claims, No Drawings

FLUORINE-CONTAINING ORGANOSILICON COMPOUNDS AND METHOD FOR THE PREPARATION THEREOF

FIELD OF THE INVENTION

The present invention relates to fluorine-containing organosilicon compounds and to a method for the preparation thereof. More specifically, the present invention relates to fluorine-containing organosilicon compounds whose molecule contains a fluorine-bearing organic group and at least 2 silicon-bonded hydrogen atoms.

BACKGROUND OF THE INVENTION

Fluorine-containing organosilicon compounds have a low surface tension, excellent chemical resistance, excellent water repellency, excellent oil repellency, and excellent lubricity or slip, and for these reasons are used to treat various types of surfaces. The following are examples of such fluorine-containing organosilicon compounds that have already been proposed:
fluorine-containing organosilicon compounds such as 3,3,3-trifluoropropylmethyldichlorosilane, 3,3,4,4,4-pentafluorobutylmethyldichlorosilane, 3,3,4,4,5,5,5-heptafluoropentylmethyldichlorosilane, 3,3,3-trifluoropropyltrichlorosilane, and so forth (Japanese Patent Application Laid Open Number Sho 50-126621); fluorine-containing organosilicon compounds such as (1-trifluoromethylethyl)methyldichlorosilane, (1-pentafluoroethylethyl)methyldichlorosilane, and so forth (Japanese Patent Application Laid Open Number Sho 57-140787; perfluoroalkylether group-containing chlorosilanes (Japanese Patent Application Laid Open Number Sho 63-255288; and perfluoroalkylether group-containing hydrogensilanes (Japanese Patent Application Laid Open Number Hei 2-115190).

In addition, the following methods have been proposed for the preparation of fluorine-containing organosilicon compounds: the execution of an addition reaction in the presence of a platinum or palladium catalyst between SiH-containing chlorosilane and olefin that contains a perfluoroalkyl group or perfluoroalkylether group (Japanese Patent Application Laid Open Numbers Sho 50-126621, Sho 57-140787, and Sho 63-255288), the reduction of a perfluoroalkylether group-containing monochlorosilane with a reducing agent, and the execution of a partial addition reaction in the presence of a platinum group metal catalyst between 1,1,3,3-tetramethyldisiloxane and perfluoroalkyl-containing olefin (the latter two in Japanese Patent Application Laid Open Number Hei 2-115190).

However, the fluorinated organic group-containing chlorosilanes proposed in Japanese Patent Application Laid Open Numbers Sho 50-126621, Sho 57-140787, and Sho 63-255288 produce hydrogen chloride gas as a by-product during their application, and this imposes limitations on the fields in which they may be utilized. The application of the fluorine-containing organosilicon compounds proposed in Japanese Patent Application Laid Open Number Hei 2-115190 is restricted by the fact that the subject compounds contain only 1 silicon-bonded hydrogen atom in the molecule.

In addition, the methods for the preparation of fluorine-containing organosilicon compounds that are proposed in the aforementioned patents suffer from the drawback that they cannot be used to prepare fluorine-containing organosilicon compounds whose molecule contains 2 or more silicon-bonded hydrogen atoms.

SUMMARY OF THE INVENTION

The present invention takes as an object the introduction of fluorine-containing organosilicon compounds whose molecule contains a fluorine-bearing organic group and at least 2 silicon-bonded hydrogen atoms. A further object of the present invention is the introduction of a method for the preparation of said fluorine-containing organosilicon compounds.

The present invention therefore, relates to fluorine-containing organosilicon compounds with the following general formula

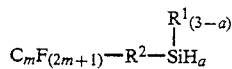

in which $R^1$ represents a monovalent hydrocarbon group, excluding alkenyl group, $R^2$ represents a divalent organic group, a is 2 or 3, and m is a number with a value of 4 to 12. The present invention also relates to a method for the preparation of the above fluorine-containing organosilicon compounds wherein said method comprises reacting (A) an organosilicon compound with the general formula

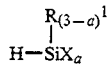

wherein $R^1$ represents a monovalent hydrocarbon group, excluding alkenyl group, X represents a halogen atom, and a is 2 or 3 and (B) a fluorine-containing organic compound with the general formula

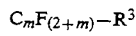

wherein $R^3$ represents a monovalent organic group that contains an aliphatically unsaturated hydrocarbon bond and m is a number with a value of 4 to 12 in the presence of (C) a hydrosilylation-reaction catalyst,
thereby producing
(D) a fluorine-containing organosilicon compound with the general formula

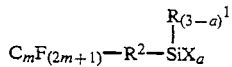

wherein the groups $R^1$ and X are defined as above, $R^2$ represents a divalent organic groups, and a and m have the values given above and then reducing said fluorine-containing organosilicon compound (D) with
(E) a reducing agent.

DETAILED DESCRIPTION OF THE INVENTION

The fluorine-containing organosilicon compounds in accordance with the present invention are represented by the following general formula.

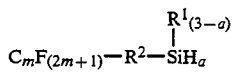

R[1] in this formula represents a monovalent hydrocarbon group, exclusive of any alkenyl group. The monovalent hydrocarbon group R[1] is specifically exemplified by alkyl groups such as methyl, ethyl, propyl, butyl, pentyl; aryl groups such as phenyl, tolyl, xylyl; and aralkyl groups such as benzyl, phenethyl. Methyl and phenyl are preferred.

R[2] in the preceding formula represents a divalent organic group. The divalent organic group R[2] is specifically exemplified by alkylene groups such as ethylene, propylene, butylene, pentylene; alkyleneoxyalkylene groups such as methyleneoxyethylene, methyleneoxypropylene, ethyleneoxypropylene; arylenealkylene groups such as phenyleneethylene, phenylenepropylene, phenylenebutylene; and aryleneoxyalkylene groups such as phenyleneoxyethylene, phenyleneoxypropylene. Ethylene and propylene are preferred.

The subscript a in the preceding formula has a value of 2 or 3. When a is 2, the fluorine-containing organosilicon compound of the present invention takes the form of a dihydrogensilane that contains a fluorinated organic group. When a is 3, the fluorine-containing organosilicon compound of the invention takes the form of a trihydrogensilane that contains a fluorinated organic group. The subscript m in the preceding formula is an integer having a value of 4 to 12. Fluorine-containing organosilicon compounds in which m is less than 4 have a poorer surface tension, chemical resistance, water repellency, oil repellency, and lubricity than fluorine-containing organosilicon compounds in accordance with the present invention. On the other hand, fluorine-containing organosilicon compounds in which m exceeds 12 are very difficult to handle and have limited applications.

No particular restrictions apply to the structure of the fluorinated organic group $-C_mF_{(2m+1)}$ that is present in the fluorine-containing organosilicon compounds in accordance with the present invention. However, this group is preferably branched, straight chain, or a partially branched straight chain. Straight chains are particularly preferred.

The fluorine-containing organosilicon compounds in accordance with the present invention as defined above are specifically exemplified by fluorine-containing organosilicon compounds with the following structures.

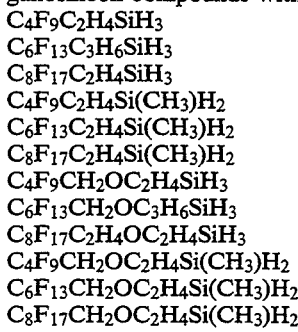

The fluorine-containing organosilicon compounds of the present invention as described above are liquids at room temperature and are easy to handle. Due to the presence of 2 or more SiH in the molecule, the fluorine-containing organosilicon compounds of the present invention are extremely reactive and are unstable in pure form. However, their storage stability can be improved by storage with the thorough exclusion of moisture. When storage of these compounds is required, they are preferably stored in plastic containers or metal cans. In addition, their storage stability is substantially improved by storage as the organic solvent solution. Organic solvents that may be used for organic solution storage of the fluorine-containing organosilicon compounds of the present invention are specifically exemplified by ether solvents such as diethyl ether, tetrahydrofuran; alkanes such as hexane, heptane; and aromatic solvents such as benzene, toluene. The solubilities of the fluorine-containing organosilicon compounds of the present invention in these organic solvents differ from those of prior art fluorine-containing organosilicon compounds.

The preparative method in accordance with the present invention characteristically comprises the execution of an addition reaction between (A) an organosilicon compound with the general formula

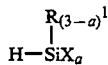

wherein R[1] represents a monovalent hydrocarbon group excluding alkenyl group, X represents a halogen atom, and a is 2 or 3 and (B) a fluorine-containing organic compound with the general formula

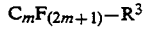

wherein R[3] represents a monovalent organic group that contain an aliphatically unsaturated hydrocarbon bond and m is a number having a value of 4 to 12 in the presence of (C) a hydrosilylation-reaction catalyst
thereby producing (D) a fluorine-containing organosilicon compound with the general formula

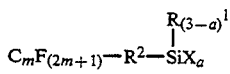

wherein the groups R[1] and X are defined as above, R[2] represents a divalent organic group, and a and m have the values given above, and the subsequent reduction of this fluorine-containing organosilicon compound (D) with (E) a reducing agent.

The organosilicon compound comprising component (A) is the main precursor in the preparative method of the present invention, and it has the following general formula.

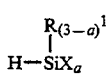

R[1] in this formula represents a monovalent hydrocarbon group, exclusive of alkenyl group. The monovalent hydrocarbon group R[1] is specifically exemplified by alkyl groups such as methyl, ethyl, propyl, butyl, pentyl; aryl groups such as phenyl, tolyl, xylyl; and aralkyl groups such as benzyl, phenethyl. The group X in the preceding formula represents a halogen atom, and is specifically exemplified by the chlorine atom and bromine atom. In addition, the subscript a in the preceding formula has a value of 2 or 3: component (A) is a dihalosilane when a=2 and is a 25 trihalosilane when a=3.

The organosilicon compounds comprising component (A) as defined above are specifically exemplified by trichlorosilane, tribromosilane, methyldichlorosilane, ethyldichlorosilane, propyldichlorosilane, phenyldichlorosilane, methyldibromosilane, ethyldibromosilane, propyldibromosilane, and phenyldibromosilane. Trichlorosilane and methyldichlorosilane are preferred as component (A).

The fluorine-containing organosilicon compound comprising component (B) in the preparative method in accordance with the present invention is the precursor that introduces the fluorinated organic group into the fluorine-containing organosilicon compound of the present invention. The fluorine-containing organosilicon compound comprising component (B) is described by the following general formula.

$$C_mF_{(2m+m)}-R^3$$

$R^3$ in the preceding formula represents a monovalent organic group that contains an aliphatically unsaturated hydrocarbon bond. The monovalent organic group comprising $R^3$ is specifically exemplified by alkenyl groups such as vinyl, allyl, butenyl, 20 pentenyl; alkenyloxyalkylene groups such as vinyloxymethylene, allyloxymethylene, allyloxyethylene; alkenylarylene groups such as styryl, allylphenylene, butenylphenylene; and alkenyloxyarylene groups such vinyloxyphenylene, allyloxyphenylene. The vinyl and allyl groups are preferred.

The subscript m in the preceding formula has a value of 4 to 12. When m is less than 4, the ultimately obtained fluorine-containing organosilicon compounds have a poorer surface tension, chemical resistance, water repellency, oil repellency, and lubricity than fluorine-containing organosilicon compounds in accordance with the present invention. On the other hand, when m exceeds 12, the ultimately obtained fluorine-containing organosilicon compounds are very difficult to handle and have limited applications.

The fluorine-containing organosilicon compounds comprising component (B) as defined hereinbefore are specifically exemplified by fluorine-containing organosilicon compounds with the following structures.

$C_6F_{13}CH_2CH=CH_2$
$C_8F_{17}CH=CH_2$
$C_4F_9CH=CH_2$
$C_6F_{13}CH=CH_2$
$C_8F_{17}CH_2CH=CH_2$
$C_4F_9CH_2OCH=CH_2$
$C_6F_{13}CH_2OCH_2CH=CH_2$
$C_8F_{17}C_2H_4OCH=CH_2$
$C_4F_9CH_2OCH_2CH=CH_2$
$C_6F_{13}CH_2OCH=CH_2$
$C_8F_{17}CH_2OCH=CH_2$

The mixing ratio between components (A) and (B) is not particularly restricted in the preparative method of the present invention, but viewed from the perspective of yield, component (B) should be added in the range of 0.1 to 5.0 moles per 1 mole component (A).

The hydrosilylation-reaction catalyst comprising the component (C) in the preparative method of the present invention is a catalyst that accelerates the addition reaction between the silicon-bonded hydrogen in component (A) and the aliphatically unsaturated hydrocarbon bond in component (B). This catalyst is exemplified by catalysts based on transition metals such as palladium, rhodium, platinum, and so forth. Platinum group metal catalysts are preferred. The platinum group metal catalysts are exemplified by platinum supported on active carbon, platinum 15 supported on silica, chloroplatinic acid, alcohol solutions of chloroplatinic acid, chloroplatinic acid/olefin complexes, chloroplatinic acid/vinylsiloxane complexes, platinum black, and so forth.

The addition of component (C) is not specifically 20 restricted in the preparative method in accordance with the present invention. However, in the particular case of the use of a platinum group metal catalyst as component (C), component (C) is preferably added so as to provide 0.1 to 1,000 weight parts platinum metal, and more preferably 0.5 to 500 weight parts platinum metal, for each 1,000,000 weight parts of the total of components (A) and (B).

The preparative method of the present invention begins with the synthesis of the fluorine-containing organosilicon compound (D) with the general formula $$C_mF_{(2m+1)}-R^2-\underset{\underset{X_a}{|}}{Si}R^1_{(3-a)}$$

by addition-reacting the above-described components (A) and (B) in the presence of component (C) as described above. $R^1$ and X in the preceding formula represent the same groups as described above, and a and m in the preceding formula have the same values as described above.

The subject addition reaction can be run with or without the use of solvent. Organic solvents operable in the case of use of organic solvent are exemplified by ethers such as ethyl ether, tetrahydrofuran, dibutyl ether, diisopropyl ether, and so forth; alkanes such as hexane, heptane; and aromatic hydrocarbons such as benzene, toluene. The reaction temperature for the subject addition reaction is not particularly restricted, however, the reaction temperature should generally be in the range of 0° C. to 200° C. When the reaction is run using organic solvent, the reaction temperature will be up to the boiling point of the organic solvent. The reaction temperature is preferably in the range from room temperature to 100° C.

The fluorine-containing organosilicon compound (component (D)) synthesized by the aforesaid addition reaction is subsequently reduced with a reducing agent (E). In the preparative method in accordance with the present invention, the reducing agent comprising component (E) reduces the silicon-bonded halogen in component (D) to yield silicon-bonded hydrogen. The reducing agent comprising component (E) is specifically exemplified by lithium aluminum hydride, sodium aluminum hydride, lithium hydride, $Al(BH_4)_3$, and sodium dihydrobis(methoxyethoxy)aluminate.

The reduction of component (D) in the preparative method of the present invention is preferably run in organic solvent. Organic solvents operable for this purpose are specifically exemplified by ethers such as ethyl ether, tetrahydrofuran, dibutyl ether, diisopropyl ether; alkanes such as hexane, heptane; and aromatic hydrocarbons such as benzene, toluene. The reaction temperature in this reaction is generally in the range of 0° C. to 80° C. The salt by-product produced along with the reaction product may be filtered off or washed out with water.

Component (E) must be added in the preparative method of the present invention in an amount that provides at least an equivalent quantity of hydride in component (E) with reference to the silicon-bonded halogen in component (D). In general, component (E) is preferably added at from a 5% excess on an equivalent basis to a 2-fold excess on an equivalent basis.

After the reduction of component (D), the component (E) reducing agent present in excess should be deactivated (e.g. by addition of water, alcohol, or ethyl acetate). Component (E) is preferably deactivated with[1] water because this facilitates removal of the resulting product after component (E) deactivation.

The fluorine-containing organosilicon compounds in accordance with the present invention are novel compounds whose molecule contains a fluorinated organic group and at least 2 silicon-bonded hydrogen atoms. Because these compounds contain 2 or more reactive silicon-bonded hydrogens, they are useful as intermediates for various types of organic materials and as starting materials for the synthesis of network polymers (resins) or linear polymers that contain high levels of fluorinated organic groups. In addition, because the fluorine-containing organosilicon compounds in accordance with the present invention have lower boiling points than the analogous trialkoxysilanes, dialkoxysilanes, and trichlorosilanes, they are useful as precursors for the formation of thin coating films by chemical vapor deposition (CVD).

EXAMPLES

The present invention is explained in greater detail hereinafter through working examples.

Example 1

One mole of perfluorooctylethylene ($C_8F_{17}CH=CH_2$) and 0.3 g of a 40 weight % isopropanol chloroplatinic acid solution were placed in a reactor and heated to 85° C. while stirring. Trichlorosilane (1.2 moles) was then dripped into this system. After the completion of silane addition, the reaction solution was stirred for an additional 1 hour while holding the temperature at 90° C. Unreacted material was subsequently removed by distillation to yield 0.85 moles of perfluorooctylethyltrichlorosilane ($C_8F_{17}CH_2CH_2SiCl_3$).

Lithium aluminum hydride (6.8 g) and 220 g tetrahydrofuran were placed in a 1 L flask, and 116 g of the perfluorooctylethyltrichlorosilane prepared as above was dripped into the flask while heating and stirring. The reaction was heated under reflux for an additional 1 hour after the completion of addition. This was followed by cooling and dripping water into the reaction solution in order to deactivate the excess lithium aluminum hydride. A large volume of water was then added in order to dissolve the salt product, and the organic layer was washed with water. The organic layer was then dried over anhydrous magnesium sulfate and subsequently filtered to yield an organic solution. The product in this organic solution was submitted to analysis by gas chromatography-mass spectrometry (GC-MS), gas chromatography-infrared spectroscopy (GC-IR), $^{29}$Si nuclear magnetic resonance spectroscopy (NMR), and $^{13}$C-NMR. A single signal at $-57$ ppm was observed by $^{29}$Si-NMR. The results from $^{13}$C-NMR are reported below.

delta (ppm): $-3$ (1.0C, s, $-\underline{C}H_2-Si-$) 28 (1.0C, s, $-CH_2-\underline{C}H_2-Si-$) 105-125 (8.5C, br, $\underline{C}_8F_{17}-$)

These results confirmed the product to be perfluorooctylethyltrihydrogensilane having the formula.

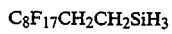

$C_8F_{17}CH_2CH_2SiH_3$

Example 2

One mole of perfluorooctylethylene ($C_8F_{17}CH=CH_2$) and 0.3 g of 40 weight % isopropanol chloroplatinic acid solution were placed in a reactor and heated to 85° C. while stirring. Methyldichlorosilane (1.3 moles) was then dripped into this system. After the completion of silane addition, the reaction solution was stirred for an additional 1 hour while holding the temperature at 90° C. Unreacted material was subsequently removed by distillation to yield 0.8 moles perfluorooctylethyl(methyl)dichlorosilane ($C_8F_{17}CH_2CH_2Si(CH_3)Cl_2$).

Lithium aluminum hydride (5.8 g) and 180 g of diethyl ether were placed in a 1 L flask, and 140 g of the perfluorooctylethyl(methyl)dichlorosilane prepared as above was dripped into the flask at room temperature. The reaction was heated under reflux for an additional 1 hour after the completion of addition. This was followed by cooling and dripping water into the reaction solution in order to deactivate the excess lithium aluminum hydride. A large volume of water was then added in order to dissolve the salt product, and the organic layer was washed with water. The organic layer was then dried over anhydrous magnesium sulfate and subsequently filtered to yield an organic solution. The product in this organic solution was submitted to analysis by GC-MS, GC-IR, $^{29}$Si-NMR, and $^{13}$C-NMR. A single signal at $-31$ ppm was observed by $^{29}$Si-NMR. The results from $^{13}$C-NMR are reported below.

delta (ppm): $-9$ (1.0C, s, $\underline{C}H_3-Si-$) 1 (1.0C, s, $-\underline{C}H_2-Si-$) 27 (1.0C, s, $-CH_2-\underline{C}H_2-Si-$) 105-125 (9.5C, br, $\underline{C}_8F_{17}-$)

These results confirmed the product to be perfluorooctylethyl(methyl)dihydrogensilane having the formula.

$C_8F_{17}CH_2CH_2Si(CH_3)H_2$

Example 3

Perfluorobutylethylene ($C_4F_9CH=CH_2$) (246 g) and 0.3 g of a 40 weight % isopropanolic chloroplatinic acid solution were placed in a reactor and heated to 55° C. while stirring. Trichlorosilane (160 g) was then dripped into this system. After the completion of silane addition, the reaction solution was stirred for an additional 1 hour while holding the temperature at 90° C. Unreacted material was subsequently removed by distillation to yield 320 g perfluorobutylethyltrichlorosilane ($C_4F_9CH_2CH_2SiCl_3$).

Lithium aluminum hydride (10.3 g) and 180 g of diethyl ether were placed in a 1 L flask, and 114 g of the perfluorobutylethyltrichlorosilane prepared as above was dripped into the flask while stirring at room temperature. The reaction was heated under reflux for an additional 1 hour after the completion of addition. This was followed by cooling and dripping water into the reaction solution in order to deactivate the excess lithium aluminum hydride. A large volume of water was then added in order to dissolve the salt product, and the organic layer was washed with water. The organic layer was then dried over anhydrous magnesium sulfate and subsequently filtered to yield an organic solution. The product in this organic solution was submitted to analysis by GC-MS, GC-IR, $^{29}$Si-NMR, and $^{13}$C-NMR. A single signal at $-57$ ppm was observed by $^{29}$Si-NMR. The results from $^{13}$C-NMR are reported below.

delta (ppm): $-3$ (1.0C, s, —$\underline{C}H_2$—Si—) 28 (1.0C, s, —CH$_2$—$\underline{C}H_2$—Si—) 105-125 (4.1C, br, $\underline{C}_4F_9$—) These results confirmed the product to be perfluorobutylethyltrihydrogensilane having the formula $$C_4F_9CH_2CH_2SiH_3.$$

That which is claimed is:

1. A fluorine-containing organosilicon compound having the general formula $$C_mF_{(2m+1)}-R^2-SiH_a^{R^1_{(3-a)}}$$

in which $R^1$ represents a monovalent hydrocarbon group, excluding alkenyl group, $R^2$ represents a divalent organic group, a is 2 or 3, and m is an integer having a value of 4 to 12.

2. The organosilicon compound according to claim 1, wherein $R^1$ is selected from the group consisting of methyl radical and phenyl radical.

3. The organosilicon compound according to claim 2, wherein $R^2$ is selected from the group consisting of ethylene and propylene groups.

4. The organosilicon compound according to claim 1, wherein $R^2$ is selected from the group consisting of ethylene and propylene groups.

5. The organosilicon compound according to claim 1, wherein said compound is represented by a formula selected from the group consisting of
$C_4F_9C_2H_4SiH_3$,
$C_6F_{13}C_3H_6SiH_3$,
$C_8F_{17}C_2H_4SiH_3$,
$C_4F_9C_2H_4Si(CH_3)H_2$,
$C_6F_{13}C_2H_4Si(CH_3)H_2$,
$C_8F_{17}C_2H_4Si(CH_3)H_2$,
$C_4F_9CH_2OC_2H_4SiH_3$,
$C_6F_{13}CH_2OC_3H_6SiH_3$,
$C_8F_{17}C_2H_4OC_2H_4SiH_3$,
$C_4F_9CH_2OC_2H_4Si(CH_3)H_2$,
$C_6F_{13}CH_2OC_2H_4Si(CH_3)H_2$ and
$C_8F_{17}CH_2OC_2H_4Si(CH_3)H_2$.

6. A method for the preparation of a fluorine-containing organosilicon compound having the general formula $$C_mF_{(2m+1)}-R^2-SiH_a^{R^1_{(3-a)}}$$

comprising reacting
(A) an organosilicon compound having the general formula $$H-SiX_a^{R^1_{(3-a)}}$$

and
(B) a fluorine-containing organic compound having the general formula $$C_mF_{(2m+1)}-R^3$$

in the presence of
(C) a hydrosilylation-reaction catalyst, thereby producing
(D) a fluorine-containing organosilicon compound having the general formula $$C_mF_{(2m+1)}-R^2-SiX_a^{R^1_{(3-a)}}$$

and subsequently reducing said fluorine-containing organosilicon compound (D) with
(E) a reducing agent,
wherein $R^1$ represents a monovalent hydrocarbon group, excluding alkenyl group, $R^2$ represents a divalent organic group, a is 2 or 3, m is an integer having a value of 4 to 12, $R^3$ represents a monovalent organic group that contain an aliphatically unsaturated hydrocarbon bond and X denotes a halogen radical.

7. The method according to claim 6, wherein X of said organosilicon compound (A) is Cl.

8. The method according to claim 7, wherein $R^1$ is selected from the group consisting of methyl radical and phenyl radical.

9. The method according to claim 8, wherein $R^3$ is selected from the group consisting of vinyl and allyl radicals.

10. The method according to claim 6, wherein said organosilicon compound (A) is selected from the group consisting of trichlorosilane, tribromosilane, methyldichlorosilane, ethyldichlorosilane, propyldichlorosilane, phenyldichlorosilane, methyldibromosilane, ethyldibromosilane, propyldibromosilane and phenyldibromosilane and said fluorine-containing organic compound (B) is represented by a formula selected from the group consisting of
$C_6F_{13}CH_2CH=CH_2$,
$C_8F_{17}CH=CH_2$,
$C_4F_9CH=CH_2$,
$C_6F_{13}CH=CH_2$,
$C_8F_{17}CH_2CH=CH_2$,
$C_4F_9CH_2OCH=CH_2$,
$C_6F_{13}CH_2OCH_2CH=CH_2$,
$C_8F_{17}C_2H_4OCH=CH_2$,
$C_4F_9CH_2OCH_2CH=CH_2$,
$C_6F_{13}CH_2OCH=CH_2$ and
$C_8F_{17}CH_2OCH=CH_2$.

11. The method according to claim 6, wherein said catalyst (C) is a platinum group metal catalyst.

12. The method according to claim 11, wherein said reducing agent (E) is lithium aluminum hydride.

* * * * *